(12) United States Patent
Tang (10) Patent No.: US 9,146,036 B2
(45) Date of Patent: Sep. 29, 2015

(54) STONE BURNER FOR A FRAGRANCE LAMP (71) Applicant: Mei & Kuang Technical Company Limited, Taipei (TW)

(72) Inventor: Kuang-Chung Tang, Taipei (TW)

(73) Assignee: Mei & Kuang Technical Company Limited, Taipei (TW)

( * ) Notice: Subject to any disclaimer, the term of this patent is extended or adjusted under 35 U.S.C. 154(b) by 392 days.

(21) Appl. No.: 13/803,306

(22) Filed: Mar. 14, 2013

(65) Prior Publication Data

US 2014/0272744 A1 Sep. 18, 2014

(51) Int. Cl.
*A61L 9/03* (2006.01)
*F23D 3/18* (2006.01)

(52) U.S. Cl.
CPC . *F23D 3/18* (2013.01); *A61L 9/037* (2013.01); *A61L 2209/12* (2013.01); *F23D 2900/00001* (2013.01); *F23D 2900/03081* (2013.01); *F23D 2900/03082* (2013.01)

(58) Field of Classification Search
CPC ............ F23D 3/18; F23D 2900/00001; F23D 2900/03082; F23D 2900/03081; F23D 3/40; A61L 9/037; A61L 2209/12; A61L 9/12; A61L 9/127
See application file for complete search history.

(56) References Cited

U.S. PATENT DOCUMENTS

2007/0134607 A1* 6/2007 Chen .............................. 431/299

* cited by examiner

*Primary Examiner* — Alfred Basichas
(74) *Attorney, Agent, or Firm* — Alan D. Kamrath; Kamrath IP Lawfirm, P.A.

(57) ABSTRACT

Provided is a stone burner for a fragrance lamp, which has a first socket and a base detachably connected to the first socket. The first socket has a first wall and a second wall opposite to the first wall. The base has a second socket and a body connected to the second socket. The second socket is detachably connected to the second wall of the first socket and has a hole formed in the second socket at a position proximal to the first socket and an aperture formed in the second socket at a position distal from the first socket. The hole and the aperture of the second socket are not in communication with the first wall of the first socket.

19 Claims, 7 Drawing Sheets

STONE BURNER FOR A FRAGRANCE LAMP

BACKGROUND OF THE INVENTION

1. Field of the Invention

The present invention relates to a stone burner, and particularly to a stone burner for a fragrance lamp.

2. Description of the Prior Arts

People nowadays are getting busier and living a faster paced life and therefore feeling stressed and tense frequently. One of the popular ways to relieve stress is using aromatherapy appliances to evaporate fragrant liquid into the ambient air to create a pleasant environment. After inhaling the fragrance, the user will feel relaxed and refreshed. In order to evaporate fragrant liquid, fragrance lamps, wick assemblies, and stone burners are commonly used aromatherapy appliances.

Figure 8:
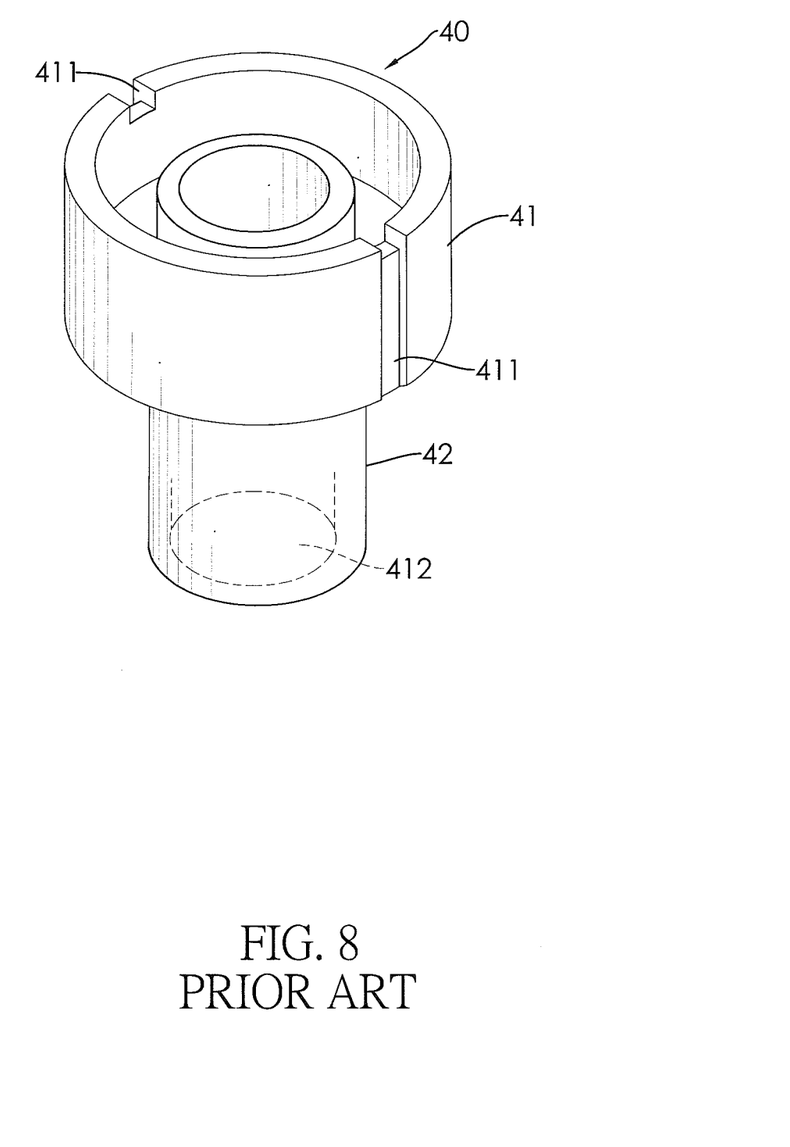
FIG. 8 is a perspective view of a stone burner in accordance with the prior art.

With reference to FIG. 8, a conventional stone burner 40 has a socket 41, a base 42 connecting to the socket 41, and a catalytic layer coated on the surface of the socket 41. The socket 41 has two recesses 411 separately formed on two opposite sides of the socket 41. A hole 412 is formed through the middle portion the base 42. When the conventional stone burner 40 is in use, a wick assembly is connected to the conventional stone burner 40 via the hole 412 and the recesses 411, and a wick of the wick assembly is placed into a fragrance lamp containing a fragrant liquid. After the wick is soaked in the fragrant liquid containing isopropyl alcohol and essential oil or containing alcohol and essential oil, the top of the socket 41 of the conventional stone burner 40 is then lit and a generated flame is allowed to burn for a while, and then the flame is extinguished. Because the catalytic layer is coated on the surface of the socket 41, the conventional stone burner 40 can remain at a high temperature after the flame is extinguished. Also, because the socket 41 and base 42 of the conventional stone burner 40 are made of ceramic, which is a porous material, the fragrant liquid can evaporate and diffuse continuously through the pores of the ceramic and scents the environment.

However, because fragrant liquids produced by different manufacturers vary in their compositions, viscosity of each fragrant liquid is also different, and thus a stone burner's degrees of saturation with each fragrant liquid are also different after each fragrant liquid is soaked by the wick and transferred to the stone burner through capillary action. As a result, if the user does not select a stone burner made of ceramic with an appropriate pore size and pore density that matches the particular fragrant liquid in use, the unsuitable stone burner is prone to over-saturation with the fragrant liquid due to a low viscosity of the fragrant liquid, resulting in that the stone burner is difficult to be lit or a flame on the stone burner is easily extinguished. Thus, the stone burner fails to scent the environment.

Accordingly, when the user buys fragrant liquids with various compositions, a conventional stone burner is not applicable to each kind of fragrant liquid. The user needs to buy different stone burners made of different ceramic materials and try to figure out which stone burner is applicable to absorb the fragrant liquid in use, which is the greatest disadvantage of the conventional stone burner.

To overcome the shortcomings, the present invention provides a stone burner for a fragrance lamp to mitigate or obviate the aforementioned problems.

SUMMARY OF THE INVENTION

Given that the aforesaid drawbacks of the prior art such as not being applicable to all kinds of fragrant liquids each containing different compositions and thus troubles the user, the main objective of the present invention is to provide a stone burner for a fragrance lamp, which comprises:

a first socket comprising:
   a first wall;
   a second wall opposite to the first wall; and
   an annular wall extending from the first wall to the second wall;
a base detachably connected to the first socket, the base comprising:
   a second socket detachably connected to the second wall of the first socket, the second socket comprising:
      a hole formed in an upper surface of the second socket proximal to the first socket;
      an aperture formed in a lower surface of the second socket distal from the first socket, the aperture in communication with the hole; and
   a body connected to the second socket comprising an opening formed through the body at a position corresponding to the aperture of the second socket, the opening in communication with the aperture and the hole;
wherein the hole and the aperture of the second socket are not in communication with the first wall of the first socket.

Preferably, the base and the first socket are made of ceramic.

More preferably, the first socket comprises a layer of ceramic and a layer of catalyst coated on a surface of the layer of ceramic. The layer of catalyst can keep the stone burner for a fragrance lamp at a high temperature after the flame is extinguished. The layer of catalyst can be, but is not limited to, platinum.

According to the present invention, the term "the hole and the aperture of the second socket are not in communication with the first wall of the first socket" refers to that the first socket does not have any space formed through the first socket at a position corresponding to the hole of the second socket, whereby the opening and the aperture are not directly in communication with an environment above the first wall of the first socket in a direction from the opening to the aperture.

According to the present invention, the shape of the first socket and the shape of the second socket are arbitrary, such as in the shape of, but not limited to, a polygonal column or cylinder.

According to the present invention, the shape of the body is arbitrary, such as in the shape of, but not limited to, a polygonal column or cylinder.

According to the aforementioned structure, the advantages of the stone burner for a fragrance lamp in accordance with the present invention are as follows:

1. The base is detachably connected to the first socket, which indicates that the base and the first socket are not integrally formed and thus the base is not in tight conjunction with the first socket, that is, the base is not seamlessly connected to the first socket, such that the first socket is not prone to saturation with the fragrant liquid when the stone burner for a fragrance lamp is in use. As a result, even a fragrant liquid with a lower viscosity is in use, the stone burner for a fragrance lamp is still lit easily and the generated flame is not easily extinguished and thus the stone burner for a fragrance lamp of the present invention is applicable to all kinds of fragrant liquids.

2. Because the hole and the aperture of the second socket are not in communication with the first wall of the first socket, an evaporated fragrant liquid can be kept in the hole of the second socket when the stone burner for a fragrance lamp is in use, and then the evaporated fragrant liquid can slowly diffuse through the pores of the ceramic, thereby extending the time of diffusing a fragrant liquid under a small amount of the fragrant liquid. Accordingly, the user can use less amount of a fragrant liquid that contains costly essential oil and thus save expenses for purchasing fragrant liquids.

Preferably, the annular wall has two opposite sides and two positioning grooves respectively formed on the two opposite sides of the annular wall; and the second socket has two opposite sides and two engaging slots respectively formed on the two opposite sides of the second socket and at positions corresponding to the positioning grooves.

When the stone burner for a fragrance lamp of the present invention is in use, each engaging slot is in communication with one of the positioning grooves when the first socket is connected to the base.

Preferably, the first wall has a central wall and a periphery wall formed around the central wall, and the periphery wall has two opposite sides and two positioning slots respectively formed on the two opposite sides of the periphery wall and corresponding to the positioning grooves, and the central wall is between the positioning slots.

When the stone burner for a fragrance lamp of the present invention is in use, each positioning slot is in communication with one of the positioning grooves when the first socket is connected to the base.

More preferably, a distance from the central wall to the second wall is shorter than a distance from the periphery wall to the second wall such that the central wall defines a recess.

According to the aforementioned structure, the shape of the recess in a cross section is arbitrary, such as, but not limited to, polygonal or circular. More preferably, the cross sectional shape of the recess i corresponds to the shape of the first socket. For example, when the first socket is a pentagonal column, the cross sectional shape of the recess is pentagonal.

Preferably, the first socket has a positioning element formed on the second wall, and the second socket has a fixing element formed on the upper surface of the second socket proximal to the first socket and at a position corresponding to the positioning element, wherein the shape of the positioning element corresponds to the shape of the fixing element.

According to the present invention, the stability of the first socket connected to the base is enhanced through the positioning element of the first socket engaging with the fixing element of the second socket.

Other objectives, advantages and novel features of the invention will become more apparent from the following detailed description when taken in conjunction with the accompanying drawings.

DETAILED DESCRIPTION OF THE PREFERRED EMBODIMENTS

For a better understanding about the technical features of the present invention and its effect, and for implements in accordance with the disclosures of the specification, preferred embodiment, details and figures are further shown as follows:

First Embodiment

Figure 1:
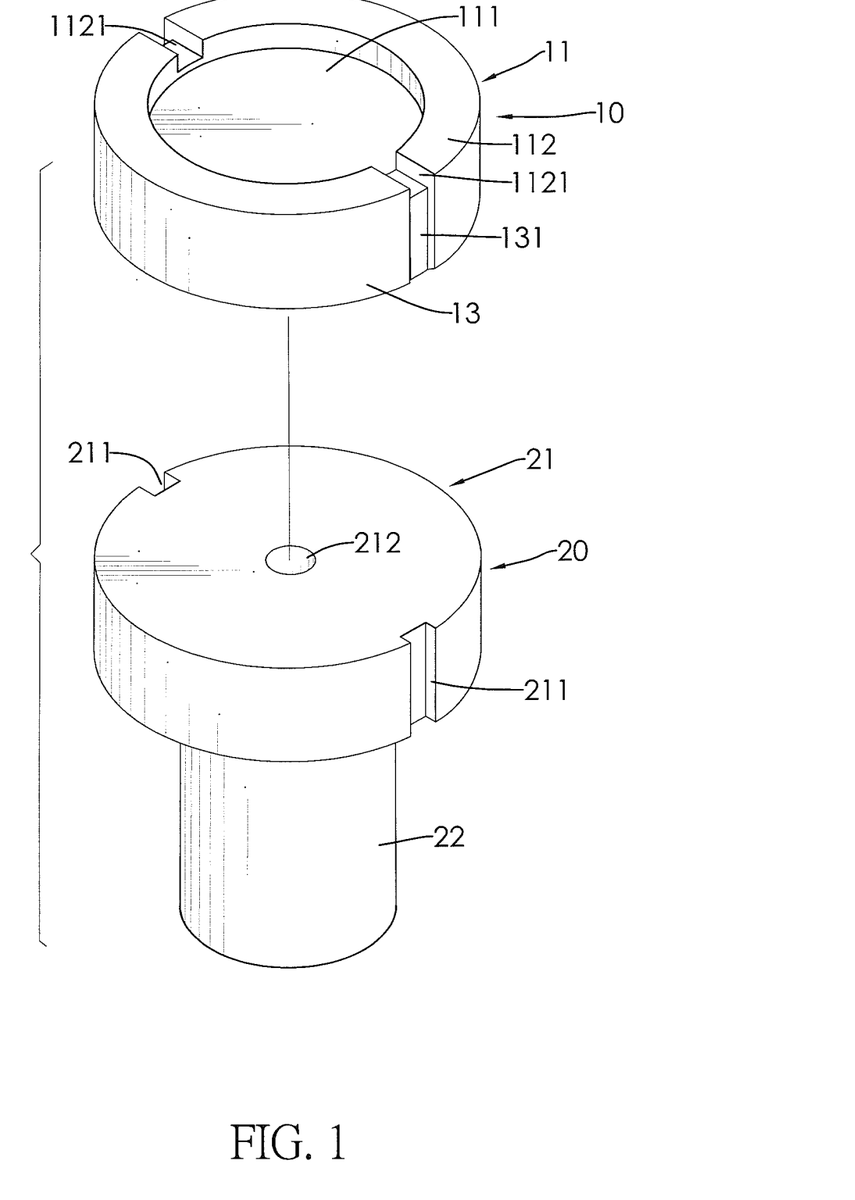
FIG. 1 is a perspective view of a first embodiment of the stone burner for a fragrance lamp in accordance with the present invention.
Figure 2:
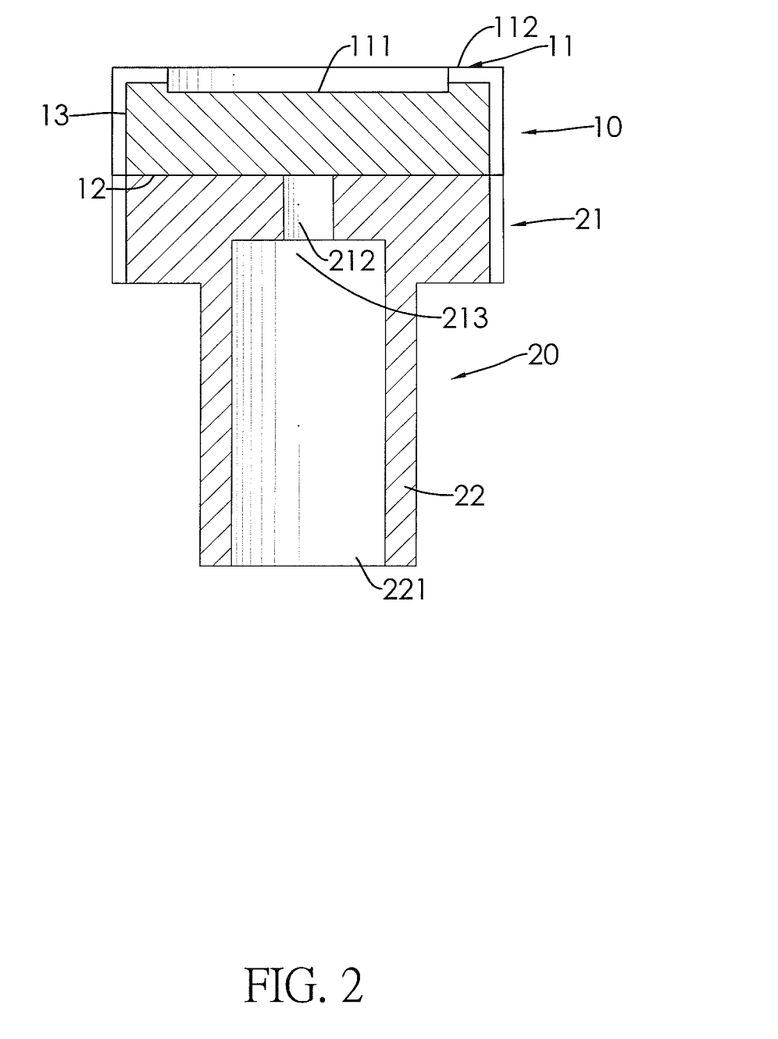
FIG. 2 is a cross sectional view of the first embodiment of the stone burner for a fragrance lamp in accordance with the present invention.

With reference to FIG. 1 and FIG. 2, the first embodiment of the stone burner for a fragrance lamp in accordance with the present invention has a first socket 10 and a base 20 detachably connected to the first socket 10.

The shape of the first socket 10 is cylindrical. The first socket 10 has a first wall 11, a second wall 12 opposite to the first wall 11, and an annular wall 13 extending from the first wall 11 to the second wall 12. The first wall 11 comprises a central wall 111 and a periphery wall 112 formed around the central wall 111. The distance from the central wall 111 to the second wall 12 is shorter than the distance from the periphery wall 112 to the second wall 12 such that the central wall 111 defines a recess. The shape of the recess in a cross section is circular. The periphery wall 112 has two opposite sides and two positioning slots 1121 respectively formed on the two opposite sides of the periphery wall 112, and the central wall 111 is between the two positioning slots 1121. The annular wall 13 has two opposite sides and two positioning grooves 1131 respectively formed on the two opposite sides and at positions corresponding to the positioning slots 1121, and each positioning groove 1131 is in communication with one of the positioning slots 1121. The first socket 10 comprises a layer of ceramic and a layer of catalyst coated on a surface of the layer of ceramic. The layer of catalyst can keep the stone burner for a fragrance lamp at a high temperature after the flame is extinguished.

The material of the base 20 is ceramic, and the base 20 has a second socket 21 and a body 22 connected to the second socket 21. The second socket 21 is detachably connected to the second wall 12 of the first socket 10, and the shape of the second socket 21 corresponds to the shape of the first socket 10, that is, the first and second sockets are both cylindrical in shape, and the diameter of the second socket 21 is substantially equal to the diameter of the first socket 10. The second socket 21 has two opposite sides, two engaging slots 211, a hole 212, and an aperture 213. The two engaging slots 211 are respectively formed on the two opposite sides of the second socket 21 and at positions corresponding to the positioning grooves 1131. When the first socket 10 is connected to the base 20, each engaging slot 211 is in communication with one of the positioning grooves 1131. The hole 212 is formed in an upper surface of the second socket 21 proximal to the first socket 10. The aperture 213 is formed in a lower surface of the second socket 21 distal from the first socket 10. The hole 212 is in communication with the aperture 213 and the diameter of the aperture 213 is larger than the diameter of the hole 212.

The body 22 is a cylinder, and the diameter thereof is smaller than the diameter of the second socket 21. The body 22 has an opening 221 formed through the body 22 at a position corresponding to the aperture 213 of the second socket 21, and the opening 221 is in communication with the aperture 213 and the hole 212 of the second socket 21. The diameter of the opening 221 is substantially equal to the diameter of the aperture 213 of the second socket 21. More specifically, when the first socket 10 is connected to the base 20, the hole 212, the aperture 213 of the second socket 21, and the opening 221 of the body 22 are not in communication with the first wall 11 of the first socket 10.

Second Embodiment

Figure 3:
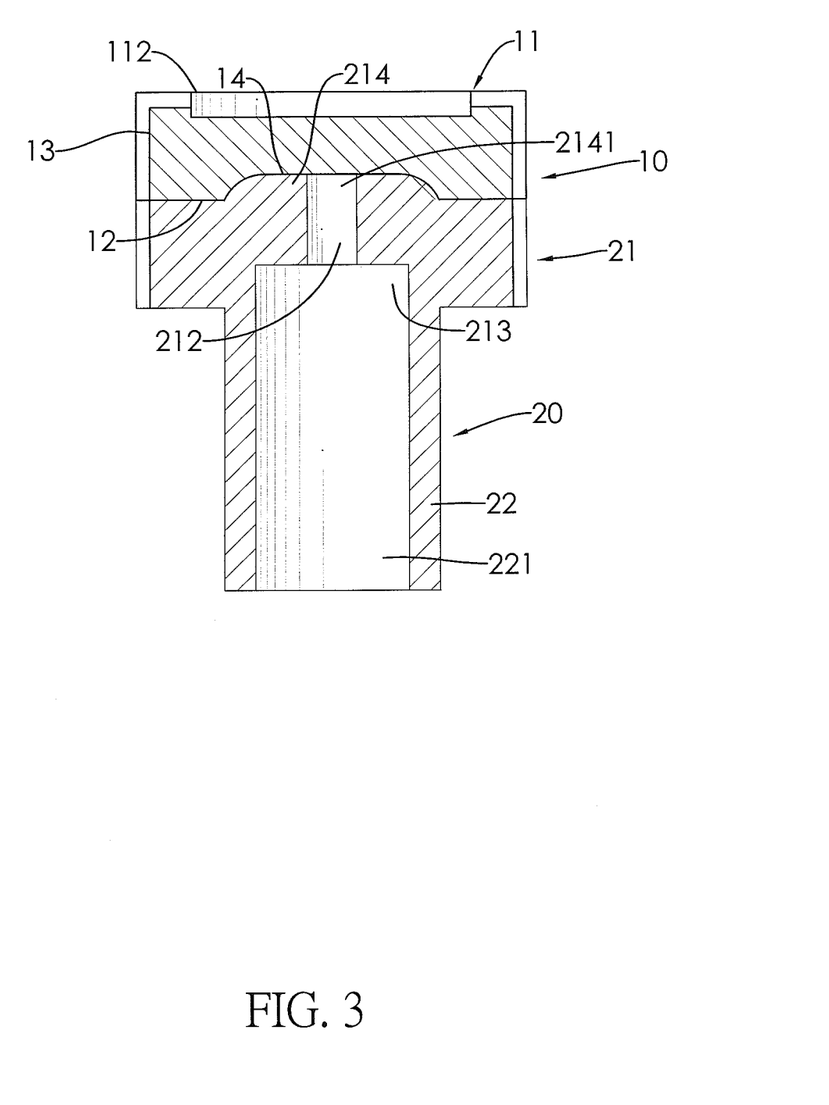
FIG. 3 is a cross sectional view of a second embodiment of the stone burner for a fragrance lamp in accordance with the present invention.

With reference to FIG. 3, the second embodiment of the stone burner for a fragrance lamp in accordance with the present invention is approximately the same as the first embodiment. The major difference is that the first socket 10 has a positioning element, which is a positioning recess 14 formed on the second wall 12 at a position corresponding to the central wall 111, and the second socket 21 has a fixing element, which is a fixing protrusion 214 protruding from the upper surface of the second socket 21 proximal to the first socket 10 and at a position corresponding to the positioning recess 14. The shape of the fixing protrusion 214 corresponds to the shape of the positioning recess 14. The fixing protrusion 214 engages with the positioning recess 14 when the base 20 is connected to the first socket 10. The fixing protrusion 214 has a cavity 2141 formed through the fixing protrusion 214 at a position corresponding to the hole 212 of the second socket 21, and the cavity 2141 is in communication with the hole 212 and the aperture 213 of the second socket 21. The diameter of the cavity 2141 is equal to the diameter of the hole 212. The stability of the first socket 10 connected to the base 20 is enhanced by the positioning recess 14 of the first socket 10 engaging with the fixing protrusion 214 of the second socket 21.

Third Embodiment

Figure 4:
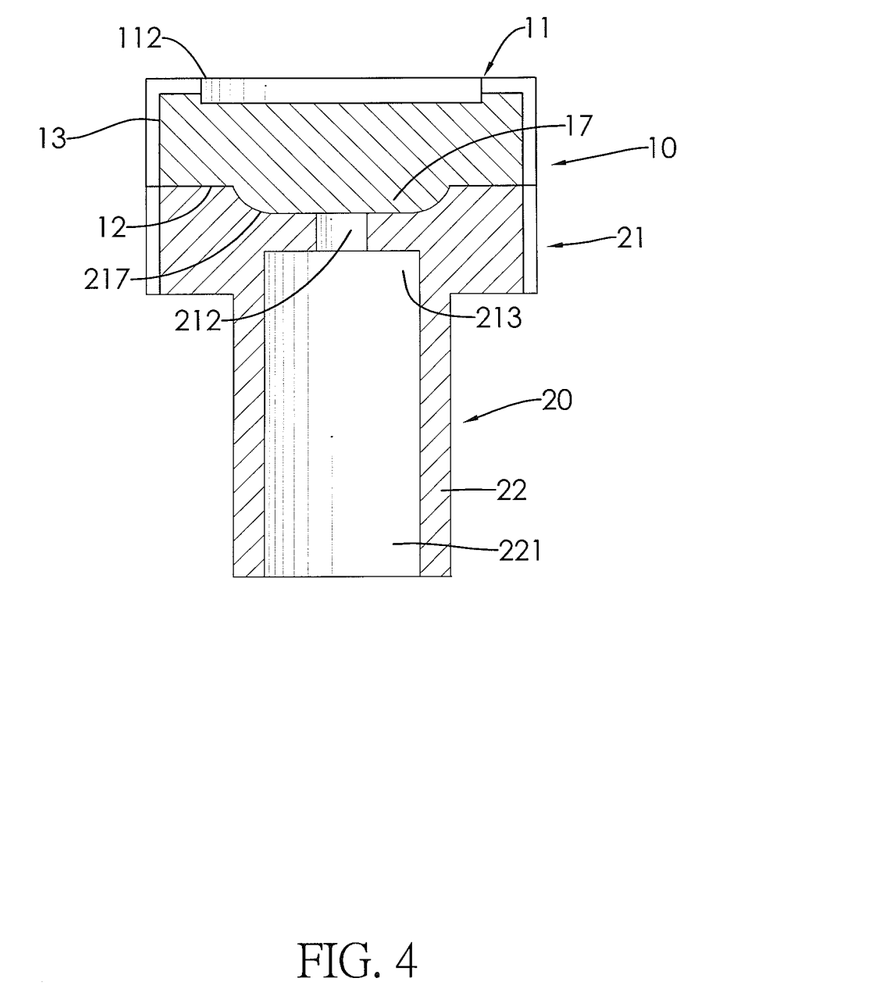
FIG. 4 is a cross sectional view of a third embodiment of the stone burner for a fragrance lamp in accordance with the present invention.

With reference to FIG. 4, the third embodiment of the stone burner for a fragrance lamp in accordance with the present invention is approximately the same as the first embodiment. The major difference is that the first socket 10 has a positioning element, which is a positioning protrusion 17 protruding from the second wall 12 at a position corresponding to the central wall 111, and the second socket 21 has a fixing element, which is a fixing recess 217 formed on the upper surface of the second socket 21 proximal to the first socket 10 and at a position corresponding to the positioning protrusion 17. The shape of the positioning protrusion 17 corresponds to the shape of the fixing recess 217. The positioning protrusion 17 engages with the fixing recess 217 to enhance stability when the base 20 is connected to the first socket 10.

Fourth Embodiment

Figure 5:
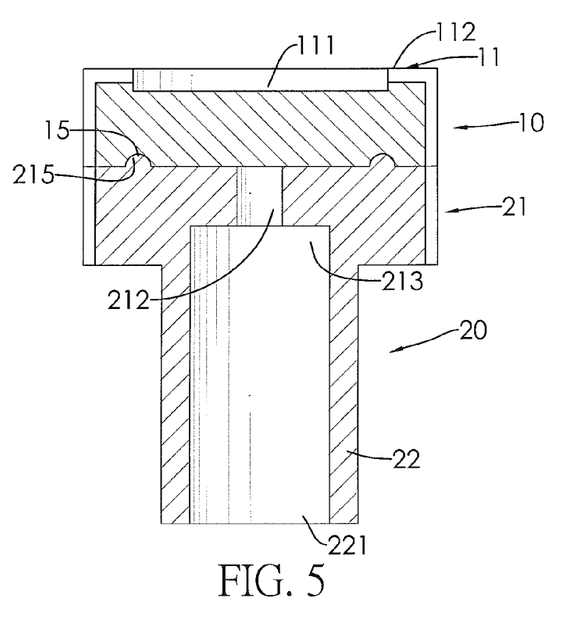
FIG. 5 is a cross sectional view of a fourth embodiment of the stone burner for a fragrance lamp in accordance with the present invention.

With reference to FIG. 5, the fourth embodiment of the stone burner for a fragrance lamp in accordance with the present invention is approximately the same as the first embodiment. The major difference is that the first socket 10 has a positioning element, which comprises two opposite positioning holes 15 formed on the second wall 12 at positions proximal to the annular wall 13, and the second socket 21 has a fixing element, which comprises two fixing bulges 215 protruding from the upper surface of the second socket 21 proximal to the first socket 10 and at positions respectively corresponding to the positioning holes 15, and the hole 212 is between the fixing bulges 215. A shape of the fixing bulges 215 corresponds to the shape of the positioning holes 15. The positioning holes 15 engage with the fixing bulges 215 respectively to enhance stability when the base 20 is connected to the first socket 10.

Fifth Embodiment

Figure 6:
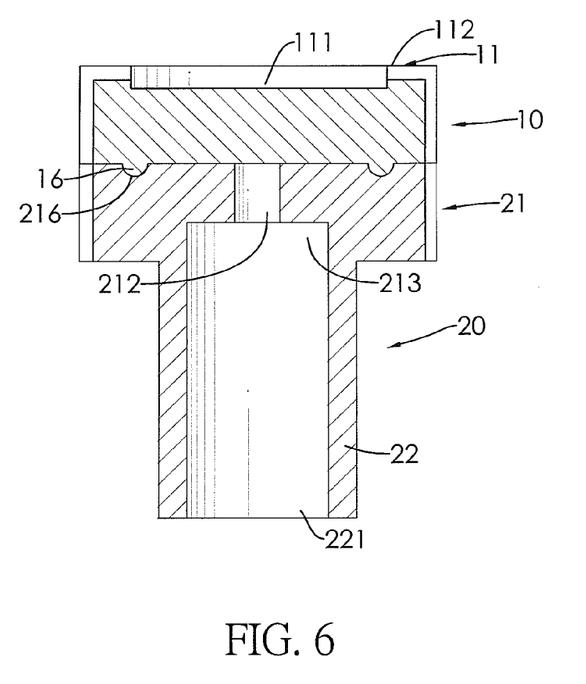
FIG. 6 a cross sectional view of a fifth embodiment of the stone burner for a fragrance lamp in accordance with the present invention.

With reference to FIG. 6, the fifth embodiment of the stone burner for a fragrance lamp in accordance with the present invention is approximately the same as the first embodiment. The major difference is that the first socket 10 has a positioning element, which comprises two opposite positioning bulges 16 protruding from the second wall 12 at positions proximal to the annular wall 13, and the second socket 21 has a fixing element, which comprises two fixing holes 216 formed on the upper surface of the second socket 21 proximal to the first socket 10 and at positions respectively corresponding to the positioning bulges 16, and the hole 212 is between the fixing holes 216. A shape of the fixing holes 216 corresponds to the shape of the positioning bulges 16. The fixing holes 216 engage with the positioning bulges 16 respectively to enhance stability when the base 20 is connected to the first socket 10.

Figure 7:
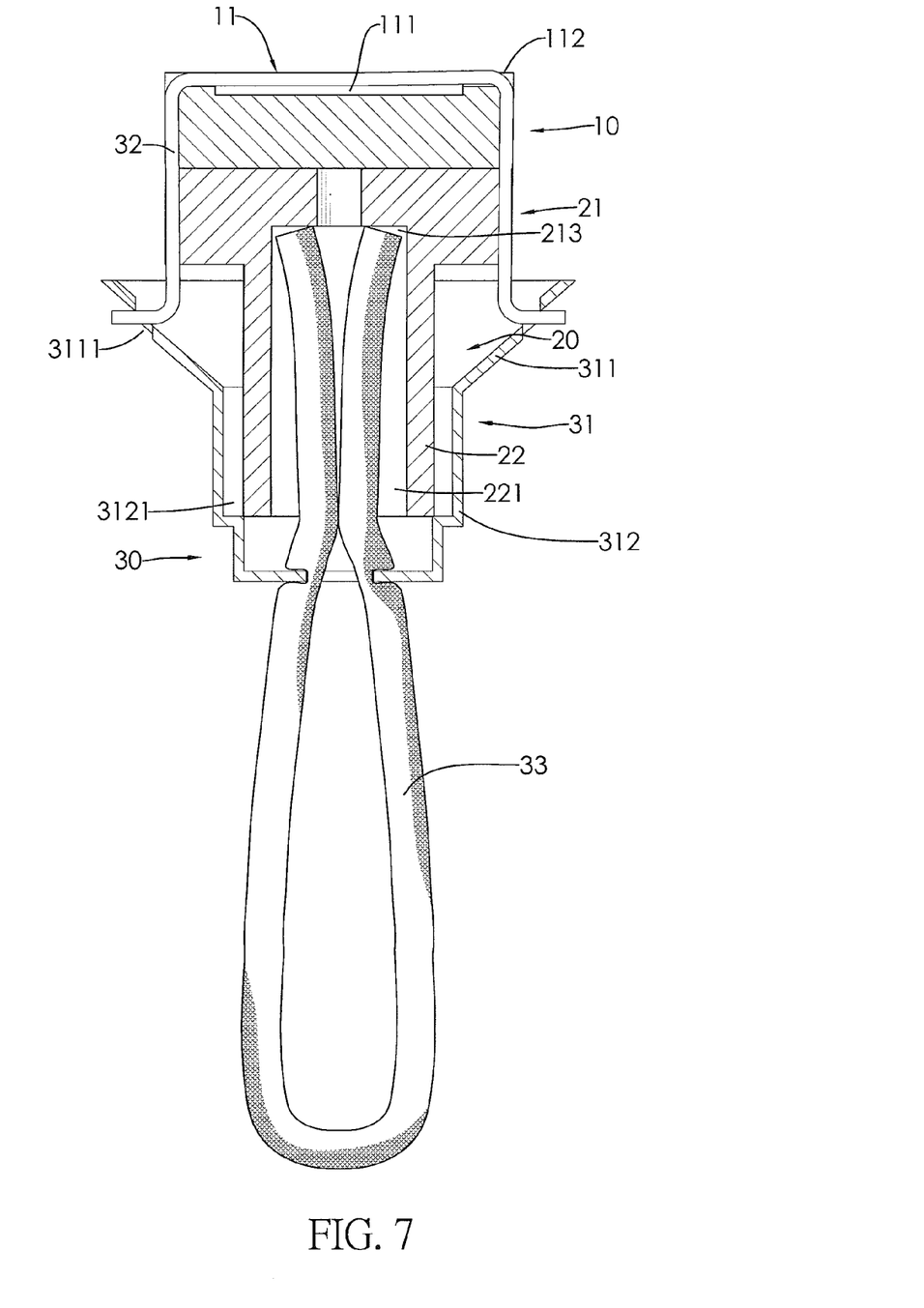
FIG. 7 is operational cross sectional view of the first embodiment of the stone burner for a fragrance lamp in accordance with the present invention.

With reference to FIG. 7, when in use, the first embodiment of the stone burner for a fragrance lamp in accordance with the present invention is connected to a wick assembly 30. The wick assembly 30 comprises a collar 31, a retainer 32 connected to the collar 31, and a wick 33 connected to the collar 31. The collar 31 has a collar ring 311 and a collar base 312 connected to the collar ring 311. The collar ring 311 has two engaging groves 3111 formed on two opposite sides of the collar ring 311. An engaging hole 3121 is formed through the collar base 312. Two ends of the retainer 32 engage with the two engaging groves 3111 of the collar ring 311 such that the retainer 32 is connected to the collar 31. The wick 33 is inserted through the engaging hole 3121 of the collar base 32 to be connected to the collar 31.

In use, the stone burner for a fragrance lamp in accordance with the present invention is connected to the wick assembly 30. More specifically, the wick 33 is inserted through the engaging hole 3121 of the collar base 312, and is placed into the opening 221 of the body 22 and the aperture 213 of the second socket 21 such that the wick 33 is connected to the base. The retainer 32 is engaged in the recess defined by the central wall 111, the positioning slots 1121 of the periphery wall 112, the positioning grooves 131 of the annular wall 13, and the engaging slots 211 of the second socket 21, and is securely mounted in the engaging grooves 3111 of the collar ring 311 in order to stably connect the first socket 10 and the base 20 and thus stably connect the stone burner for a fragrance lamp with the wick assembly 30.

The stone burner for a fragrance lamp in accordance with the present invention comprises the first socket 10 and the base 20 detachably connected to the first socket 10, that is, the first socket 10 and the base 20 are not integrally formed. Thus, the first socket 10 is not prone to saturation with fragrant liquid because the base 20 is not in tight conjunction with the first socket 10. As a result, even a fragrant liquid with a lower viscosity is in use, the stone burner for a fragrance lamp can still be lit easily and the generated flame is not easily extinguished and thus the stone burner for a fragrance lamp of the present invention is applicable to all kinds of fragrant liquids.

Furthermore, when the stone burner for a fragrance lamp of the present invention is in use, because the hole 212 and the aperture 213 of the second socket 21 are not in communication with the first wall 11 of the first socket 10, the evaporated fragrant liquid can be kept in the hole 212 of the second socket 21 and thus will not rapidly diffuse from the first wall 11. Further, because both the material of the first socket 10 and the base 20 comprise porous ceramic, the evaporated fragrant liquid can slowly diffuse through the pores of the ceramic, thereby extending the time for diffusing a fragrant liquid under a small amount of the fragrant liquid. Accordingly, the user can use less amount of a fragrant liquid that contains costly essential oil and thus save expenses for purchasing fragrant liquids.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A stone burner for a fragrance lamp comprising:
a first socket comprising:
a first wall;
a second wall opposite to the first wall; and
an annular wall extending from the first wall to the second wall;
a base detachably connected to the first socket, the base comprising:
a second socket detachably connected to the second wall of the first socket, the second socket comprising:
a hole formed in an upper surface of the second socket proximal to the first socket;
an aperture formed in a lower surface of the second socket distal from the first socket, the aperture in communication with the hole; and
a body connected to the second socket, the body comprising an opening formed through the body at a position corresponding to the aperture of the second socket, the opening in communication with the aperture and the hole;
wherein the hole and the aperture of the second socket are not in communication with the first wall of the first socket.

2. The stone burner for a fragrance lamp according to claim 1, wherein the annular wall has two opposite sides and two positioning grooves respectively formed on the two opposite sides of the annular wall, and the second socket has two opposite sides and two engaging slots respectively formed on the two opposite sides of the second socket and at positions corresponding to the positioning grooves.

3. The stone burner for a fragrance lamp according to claim 2, wherein the first wall has a central wall and a periphery wall formed around the central wall, and the periphery wall has two opposite sides and two positioning slots respectively formed on the two opposite sides of the periphery wall and corresponding to the positioning grooves, and the central wall is between the positioning slots.

4. The stone burner for a fragrance lamp according to claim 3, wherein the first socket has a positioning element formed on the second wall, and the second socket has a fixing element formed on the upper surface of the second socket proximal to the first socket and at a position corresponding to the positioning element, and a shape of the positioning element corresponds to a shape of the fixing element.

5. The stone burner for a fragrance lamp according to claim 4, wherein the positioning element comprises a positioning recess formed on the second wall, and the fixing element comprises a fixing protrusion protruding from the upper surface of the second socket proximal to the first socket and at a position corresponding to the positioning recess, and the fixing protrusion has a cavity formed through the fixing protrusion at a position corresponding to the hole of the second socket, the cavity in communication with the hole and the aperture of the second socket.

6. The stone burner for a fragrance lamp according to claim 5, wherein a diameter of the cavity is substantially equal to a diameter of the hole.

7. The stone burner for a fragrance lamp according to claim 6, wherein a diameter of the aperture is larger than the diameter of the hole.

8. The stone burner for a fragrance lamp according to claim 4, wherein the positioning element comprises a positioning protrusion protruding from the second wall at a position corresponding to the central wall, and the fixing element comprises a fixing recess formed on the upper surface of the second socket proximal to the first socket and at a position corresponding to the positioning protrusion.

9. The stone burner for a fragrance lamp according to claim 8, wherein a diameter of the aperture is larger than a diameter of the hole.

10. The stone burner for a fragrance lamp according to claim 4, wherein the positioning element comprises a positioning hole formed on the second wall, and the fixing element comprises a fixing bulge protruding from the upper surface of the second socket proximal to the first socket and at a position corresponding to the positioning hole.

11. The stone burner for a fragrance lamp according to claim 10, wherein a diameter of the aperture is larger than a diameter of the hole.

12. The stone burner for a fragrance lamp according to claim 4, wherein the positioning element comprises a positioning bulge protruding from the second wall, and the fixing element comprises a fixing hole formed on the upper surface of the second socket proximal to the first socket and at a position corresponding to the positioning bulge.

13. The stone burner for a fragrance lamp according to claim 12, wherein a diameter of the aperture is larger than a diameter of the hole.

14. The stone burner for a fragrance lamp according to claim 3, wherein a distance from the central wall to the second wall is shorter than a distance from the periphery wall to the second wall such that the central wall defines a recess.

15. The stone burner for a fragrance lamp according to claim 4, wherein a distance from the central wall to the second wall is shorter than a distance from the periphery wall to the second wall such that the central wall defines a recess.

16. The stone burner for a fragrance lamp according to claim 5, wherein a distance from the central wall to the second wall is shorter than a distance from the periphery wall to the second wall such that the central wall defines a recess.

17. The stone burner for a fragrance lamp according to claim 8, wherein a distance from the central wall to the second wall is shorter than a distance from the periphery wall to the second wall such that the central wall defines a recess.

18. The stone burner for a fragrance lamp according to claim 10, wherein a distance from the central wall to the second wall is shorter than a distance from the periphery wall to the second wall such that the central wall defines a recess.

19. The stone burner for a fragrance lamp according to claim 12, wherein a distance from the central wall to the second wall is shorter than a distance from the periphery wall to the second wall such that the central wall defines a recess.

* * * * *